US00PP31566P2

(12) United States Plant Patent
Klemm et al.

(10) Patent No.: US PP31,566 P2
(45) Date of Patent: Mar. 17, 2020

(54) ***OSTEOSPERMUM* PLANT NAMED 'KLEOE18318'**

(50) Latin Name: ***Osteospermum ecklonis* Norl.**
Varietal Denomination: KLEOE18318

(71) Applicant: Klemm+Sohn GmbH & Co. KG, Stuttgart (DE)

(72) Inventors: Nils Klemm, Stuttgart (DE); Maike Boxriker, Schwäbisch Gmünd (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/501,843

(22) Filed: Jun. 17, 2019

(51) Int. Cl.
*A01H 5/02* (2018.01)
*A01H 6/14* (2018.01)

(52) U.S. Cl.
USPC ..... Plt./360

(58) Field of Classification Search
USPC ..... Plt./360
CPC ..... A01H 5/02; A01H 6/14
See application file for complete search history.

*Primary Examiner* — Annette H Para
(74) *Attorney, Agent, or Firm* — Barbara Campbell; Cochran Freund & Young LLC

(57) ABSTRACT

A new *Osteospermum* plant particularly distinguished by yellow flowers and an upright growth habit, is disclosed.

1 Drawing Sheet

Genus and species: *Osteospermum ecklonis* Norl.
Variety denomination: 'KLEOE18318'.

BACKGROUND OF THE NEW PLANT

The present invention comprises a new and distinct variety of *Osteospermum*, botanically known as *Osteospermum ecklonis* Norl., and hereinafter referred to by the variety name 'KLEOE18318'. 'KLEOE18318' originated from a cross-pollination conducted in August to September 2012 in Stuttgart, Germany between the proprietary female *Osteospermum* variety 'OE-2011-0679' (unpatented), and the proprietary male *Osteospermum* variety 'OE-2009-0816', also known as 'KLEOE11187' (U.S. Plant Pat. No. 24,034).

The seeds from the cross were sown and plants were grown in a greenhouse for evaluation, where an individual plant designated 'KLEOE18318' was selected from the group of plants in May 2012 in Stuttgart. In June 2012 in Stuttgart, 'KLEOE18318' was first vegetatively propagated by vegetative terminal cuttings. 'KLEOE18318' was found to reproduce true to type in successive generations of asexual propagation via vegetative terminal cuttings.

SUMMARY

The following are the most outstanding and distinguishing characteristics of this new variety when grown under normal horticultural practices in Stuttgart, Germany.

1. Yellow flowers
2. An upright growth habit; and
3. Good branching.

DESCRIPTION OF THE PHOTOGRAPH

This new *Osteospermum* plant is illustrated by the accompanying photograph which shows the plant's overall plant habit including form, foliage, and flowers.

The photograph is of an 8-week-old plant grown in a greenhouse in Stuttgart, Germany in May 2019. The colors shown are as true as can be reasonably obtained by conventional photographic procedures.

DESCRIPTION OF THE NEW VARIETY

The following detailed descriptions set forth the distinctive characteristics of 'KLEOE18318'. The data which define these characteristics were collected in Latina, Italy on May 16, 2019 on plants that had been potted in week 45 of 2018 and cultivated in a plastic greenhouse. Color references are to The R.H.S. Colour Chart of The Royal Horticultural Society of London (R.H.S.), 5$^{th}$ edition (2007).

Classification:
- *Family.*—Asteraceae.
- *Botanical.*—*Osteospermum ecklonis.*
- *Common.*—*Osteospermum.*
- *Designation.*—'KLEOE18318'.

Parentage:
- *Female parent.*—The proprietary *Osteospermum* variety 'OE-2011-0679' (unpatented).
- *Male parent.*—The proprietary *Osteospermum* variety 'KLEOE11187' (U.S. Plant Pat. No. 24,034).

Plant:
- *Form and habit.*—Herbaceous perennial but usually cultivated as an annual; not frost resistant.
- *Growth habit.*—Upright.
- *Branching habit.*—Normal.
- *Height (from top of soil, including inflorescence).*—32.0 cm.
- *Width (including inflorescences).*—35.0 cm.
- *Propagation type.*—Stem cuttings; vegetative terminal tip cuttings.
- *Time to produce a finished flowering plant.*—9 weeks.
- *Time to initiate and develop roots.*—4 weeks.
- *Root description.*—Fine and white, RHS 155A.

Stems:
- *Total number of branches per plant (calculated at the base of the plant).*—9.

*Length.*—28.0 cm.
*Diameter.*—0.5 cm.
*Internode length.*—1.5 cm.
*Color.*—RHS 138B.
*Texture.*—Smooth but with fine hairs.
*Anthocyanin.*—Absent.

Leaves:
*Arrangement.*—Alternate.
*Shape.*—Obovate.
*Apex.*—Acute.
*Base.*—Acute.
*Margin.*—Entire.
*Immature color.*—Upper surface: RHS 146A. Lower surface: RHS 146B.
*Mature color.*—Upper surface: RHS 147A. Lower surface: RHS 146A.
*Length.*—5.4 cm.
*Width.*—1.8 cm.
*Texture.*—Upper surface: Leathery. Lower surface: Leathery with fine hairs.
*Petioles.*—Absent.
*Venation pattern.*—Pinnate.
*Venation color.*—Upper surface: RHS 137D. Lower surface: RHS 137C.

Flower buds:
*Shape.*—Round-ovoid.
*Length.*—1.0 cm.
*Diameter.*—1.1 cm.
*Color* (*at tight bud just before the ray florets unfold*).—RHS 137D.

Inflorescence:
*Type.*—Single.
*Blooming habit.*—Upright, with longer flower stems.
*Quantity of inflorescences per plant.*—12.
*Lastingness of the inflorescences on the plant.*—10 to 15 days.
*Fragrance.*—Present.
*Inflorescence diameter.*—7.0 cm.
*Inflorescence depth.*—1.0 cm.
*Disc diameter.*—1.3 cm.

Disc floret:
*Quantity per inflorescence.*—22.
*Shape.*—Tubular.
*Tube color.*—Closed: RHS 12A. Mature: RHS 9A.
*Length.*—0.7 cm.
*Diameter* (*at apex*).—0.2 cm.
*Apex.*—Acute.
*Apex color.*—RHS 92A.
*Base.*—Acute.
*Base color.*—RHS 10B.
*Margin.*—Entire.

Ray floret:
*Quantity per inflorescence.*—23.
*Shape.*—Oblanceolate.
*Color.*—Upper surface: RHS 12B. Lower surface: RHS 12A.
*Length.*—3.6 cm.
*Width.*—1.0 cm.
*Apex.*—Acute.
*Base.*—Acute.
*Margin.*—Entire.
*Texture.*—Upper surface: Smooth. Lower surface: Smooth, shiny.

Peduncle:
*Length.*—2.0 cm.
*Diameter.*—0.1 cm.
*Texture.*—Smooth with hairs.
*Color.*—RHS 137A.

Phyllaries:
*Arrangement.*—Single.
*Observed quantity per flower.*—16.
*Shape.*—Lanceolate.
*Apex.*—Acute.
*Base.*—Obtuse.
*Margin.*—Entire.
*Length.*—1.2 cm.
*Width.*—0.2 cm.
*Texture.*—Upper surface: Smooth with fine hairs. Lower surface: Smooth.
*Color.*—Upper surface: RHS 137C. Lower surface: RHS 139B.

Reproductive organs:
*Androecium.*—Location: On disc and ray florets. Stamens: Shape: Filamentous. Quantity: Numerous, 70 to 100. Filament length: 0.7 cm. Filament diameter: 0.1 cm. Anther: Shape: Lanceolate. Color: RHS N92A. Length: 0.2 cm. Diameter: 0.1 cm. Pollen: Color: RHS 25A. Amount: Moderate.
*Gynoecium.*—Location: On the phyllary. Pistils: Number: Numerous, 50 to 70. Length: 0.8 cm. Diameter: 0.2 cm. Stigma: Color: RHS 18D. Shape: Tapering filamentous and split in two parts. Length: 0.2 cm. Diameter: 0.2 cm. Style: Color: RHS 156D. Length: 0.4 cm. Diameter: 0.1 cm.

Fruit and seed set: None observed to date.

Disease and pest/insect resistance: No disease and pest/insect resistance observed.

COMPARISON WITH PARENTAL LINES AND KNOWN VARIETY

'KLEOE18318' is a distinct variety of *Osteospermum* and is distinguished from its parents as described in Table 1.

TABLE 1

Comparison with Parental Lines

| Characteristic | 'KLEOE18318' | Female Parent 'OE-2011-0679' | Male Parent 'OE-2009-0816' |
|---|---|---|---|
| Earliness | Early | Medium early | Medium early |
| Branching | Good | Medium | Good |

'KLEOE18318' is most similar to the commercial *Osteospermum* variety 'Flower Power Pink' (KLEOE17007). Differences between the varieties are described in Table 2.

TABLE 2

Comparison with Similar Variety

| Characteristic | 'KLEOE18318' | 'Flower Power Pink' |
|---|---|---|
| Flower color | Yellow | Pink |
| Earliness | Early | Very Early |

We claim:

1. A new and distinct variety of *Osteospermum* plant designated 'KLEOE18318' as illustrated and described herein.

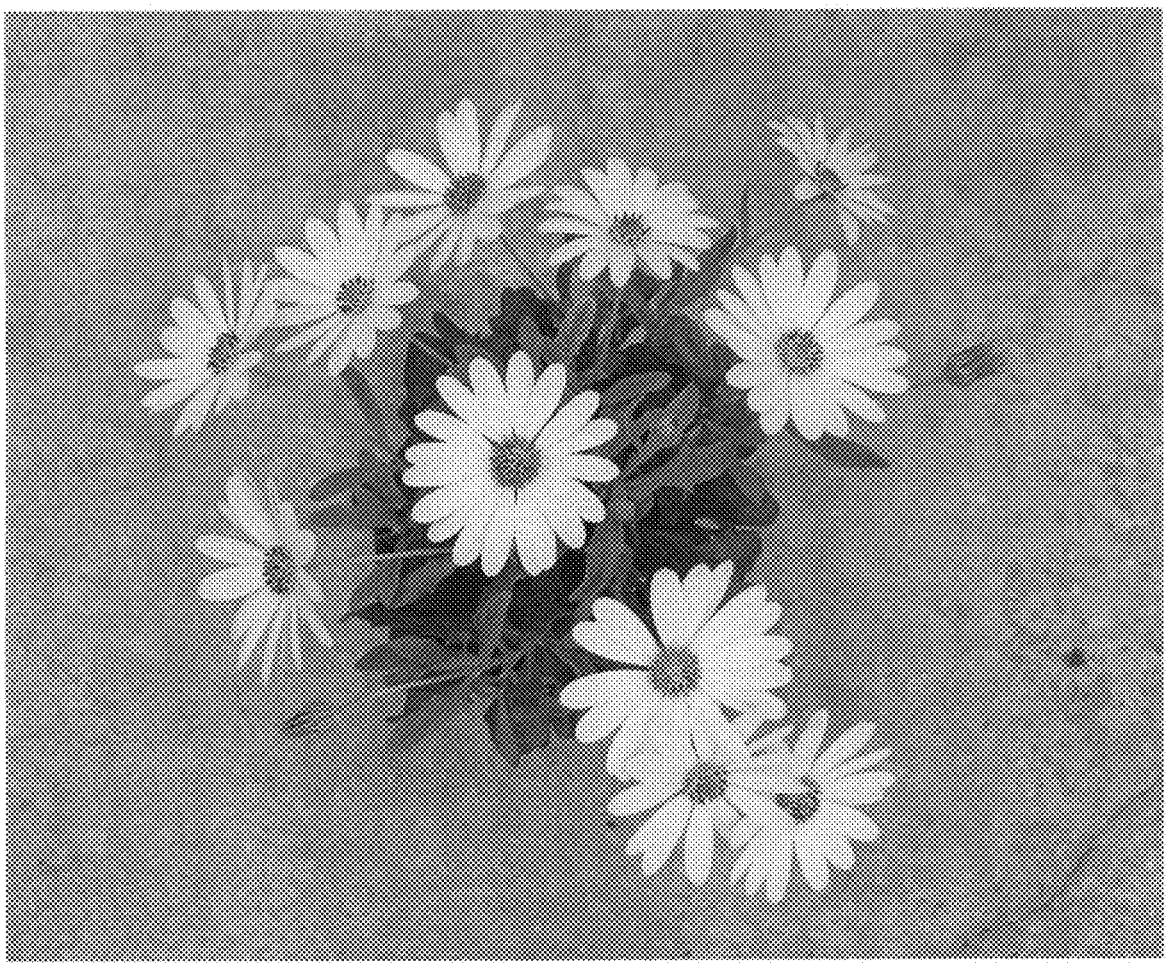

* * * * *